US012605063B2

(12) United States Patent
Sinha et al.

(10) Patent No.: US 12,605,063 B2
(45) Date of Patent: Apr. 21, 2026

(54) VISUAL ACUITY MEASUREMENT IN VR HEADSET

(71) Applicant: VERILY LIFE SCIENCES LLC, Dallas, TX (US)

(72) Inventors: Supriyo Sinha, Menlo Park, CA (US); Nick Leindecker, Portola Valley, CA (US); Jeremy Chan, San Jose, CA (US); Dimitri Azar, Chicago, IL (US)

(73) Assignee: Verily Health Inc., Dallas, TX (US)

( * ) Notice: Subject to any disclaimer, the term of this patent is extended or adjusted under 35 U.S.C. 154(b) by 566 days.

(21) Appl. No.: 18/193,193

(22) Filed: Mar. 30, 2023

(65) Prior Publication Data

US 2023/0309816 A1 Oct. 5, 2023

Related U.S. Application Data

(60) Provisional application No. 63/325,963, filed on Mar. 31, 2022.

(51) Int. Cl.
*A61B 3/028* (2006.01)
*A61B 3/00* (2006.01)
*G02B 27/01* (2006.01)
*G06F 3/01* (2006.01)

(52) U.S. Cl.
CPC ............ *A61B 3/028* (2013.01); *A61B 3/0008* (2013.01); *A61B 3/0041* (2013.01); *G02B 27/017* (2013.01); *G06F 3/013* (2013.01)

(58) Field of Classification Search
CPC ....... A61B 3/028; A61B 3/032; A61B 3/0041; G02B 27/017; G06F 3/013
USPC ....................................................... 351/222
See application file for complete search history.

(56) References Cited

U.S. PATENT DOCUMENTS

| | | | |
|---|---|---|---|
| 10,231,614 B2 | 3/2019 | Krueger | |
| 10,545,341 B2 | 1/2020 | Samec et al. | |
| 10,877,556 B2 | 12/2020 | Berkner-Cieslicki et al. | |
| 11,612,316 B2 | 3/2023 | Zidan et al. | |
| 11,696,073 B2 | 7/2023 | Spector | |
| 2009/0244485 A1* | 10/2009 | Walsh .................. A61B 3/0008 | |
| | | | 351/221 |

(Continued)

FOREIGN PATENT DOCUMENTS

| | | |
|---|---|---|
| KR | 10-1966164 B1 | 4/2019 |

OTHER PUBLICATIONS

International Search Report and Written Opinion received for PCT Patent Application No. PCT/US2023/016983, mailed on Jun. 22, 2023, 10 pages.

(Continued)

*Primary Examiner* — Stephone B Allen
*Assistant Examiner* — Boutsikaris Leonidas
(74) *Attorney, Agent, or Firm* — Christensen O'Connor Johnson Kindness PLLC

(57) ABSTRACT

A headset includes a first display, a second display that is smaller than the first display and has lower resolution than the first display, and a dichroic filter positioned to pass visible light from the first display toward the eye and reflect visible light from the second display toward the eye. Pixel data control circuitry is coupled to darken the first display while simultaneously activating the second display to display a pattern for testing visual acuity, responsive to a first visual acuity test selection. Other aspects are also described and claimed.

20 Claims, 5 Drawing Sheets

(56)         References Cited

U.S. PATENT DOCUMENTS

| 2021/0030270 | A1 | 2/2021 | Goyal et al. | |
| 2021/0089118 | A1* | 3/2021 | Jaeken | G06F 3/013 |
| 2021/0330185 | A1 | 10/2021 | Krukowski et al. | |
| 2023/0200644 | A1 | 6/2023 | Mansouri et al. | |

OTHER PUBLICATIONS

Extended European Search Report mailed Dec. 19, 2025, in corresponding EP Application No. 25218126.8, 9 pages.

* cited by examiner

VISUAL ACUITY MEASUREMENT IN VR HEADSET

CROSS-REFERENCE TO RELATED APPLICATION

This patent application claims the benefit of the earlier filing date of U.S. Provisional No. 63/325,963, filed 31 Mar. 2022.

FIELD

The subject matter of this disclosure relates to techniques for measuring visual acuity of a human user, using a virtual reality, VR, headset worn by the user.

BACKGROUND

Visual acuity is one of the most common measurements done at the office of an eye care professional (ECP). Eye examinations have been suggested to be performed with a head-worn VR unit. The user puts on the VR head unit, and the ECP operates software that configures the display inside the VR head unit to display various visual elements whose shape, color or size is selected for the test. The user provides feedback to the ECP on how they perceive the visual elements.

SUMMARY

An aspect of the disclosure here is a method for measuring visual acuity to at least the 20/20 level with an otherwise relatively standard consumer-grade VR headset that has been modified as described below. A standard consumer-grade VR headset does not have sufficient full frame pixel resolution in its display to measure acuity close to the 20/20 level. In accordance with one aspect of the disclosure here, central visual acuity of the wearer can be performed using the following system. A headset includes a first display, a second display that is smaller than the first display and has lower pixel count than the first display, and a dichroic filter positioned to pass visible light from the first display toward the eye and reflect visible light from the second display toward the eye. Pixel data control circuitry is coupled to darken the first display while simultaneously activating the second display to display a pattern for testing visual acuity, responsive to a first visual acuity test selection.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings, in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

Figure 1:
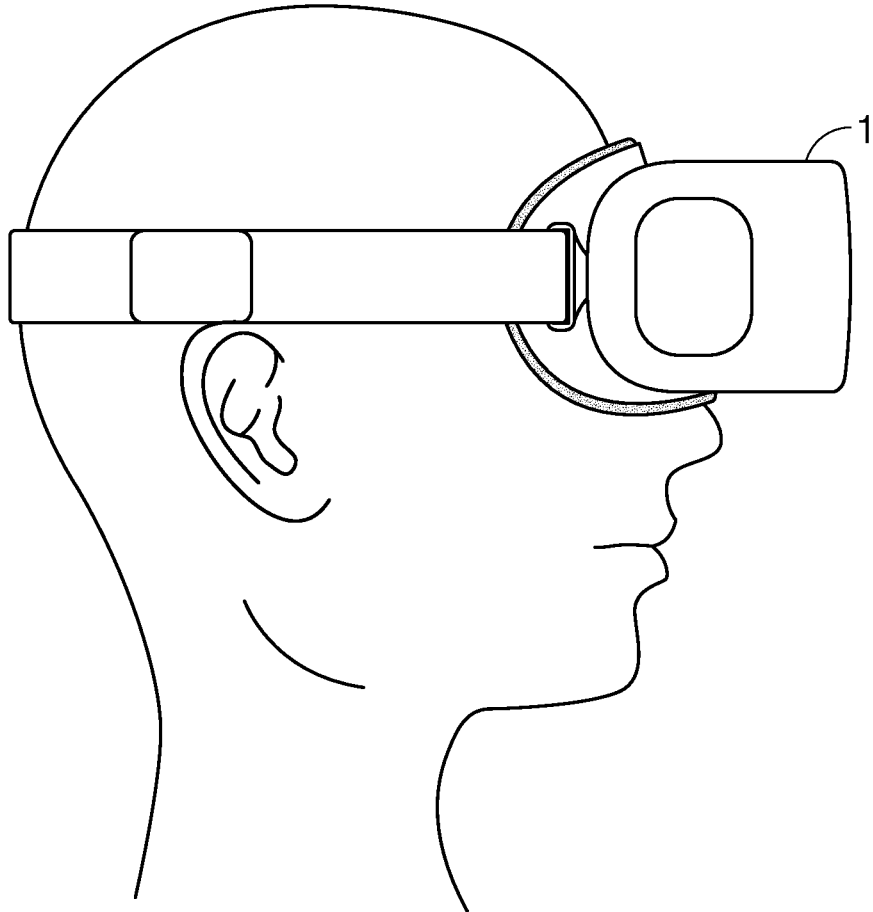
FIG. 1 depicts a user wearing a VR headset.

FIG. 1 depicts a user (wearer) wearing a virtual reality, VR, headset which as modified below can be used to perform various ophthalmic examinations on the eyes of the wearer, including visual acuity testing for 20/20 vision or better. The modifications enable the use of a relatively low-cost solution in the form of an otherwise consumer grade VR headset.

Figure 2:
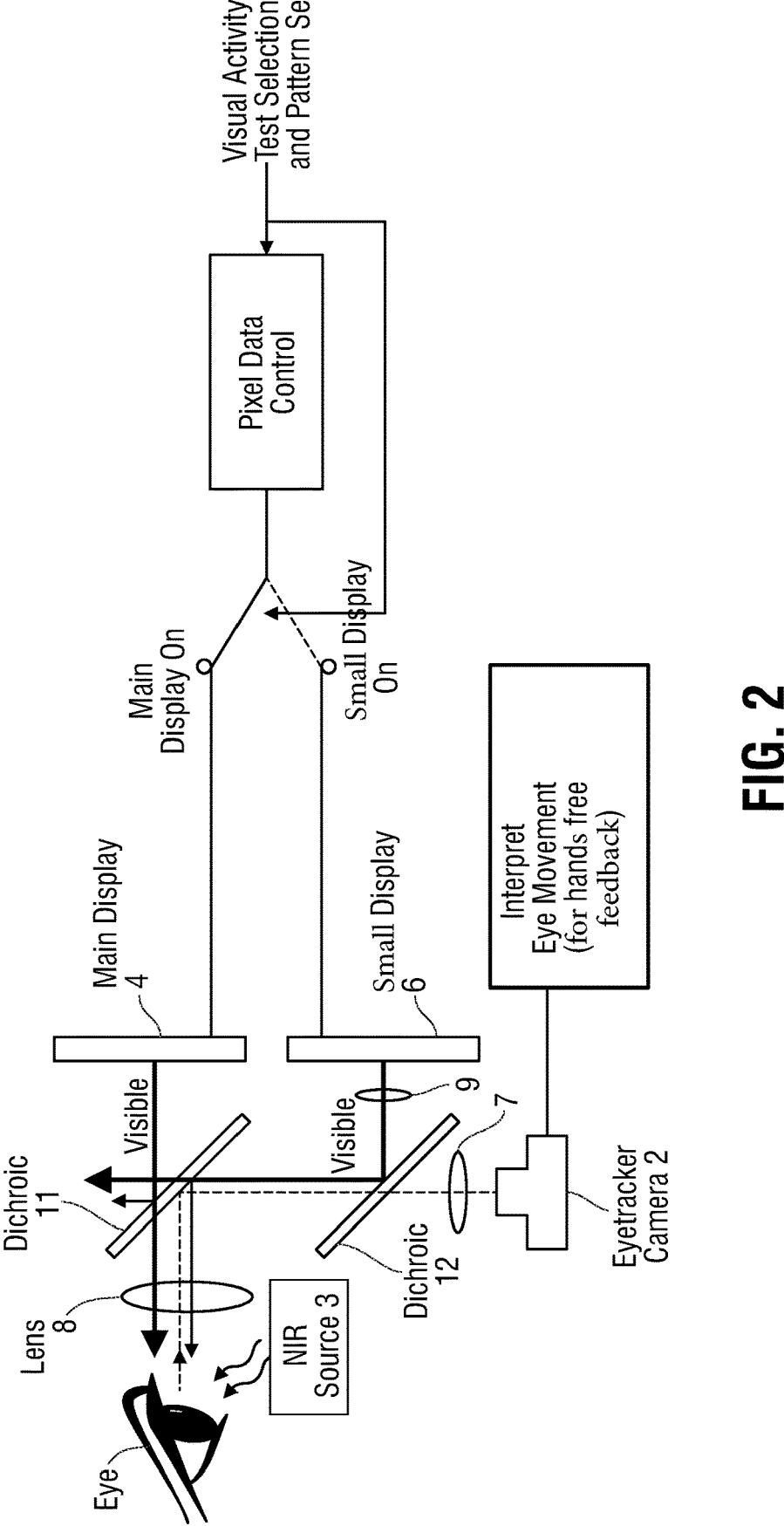
FIG. 2 is a block diagram of an example system for measuring visual acuity using a VR headset that has an eye tracker camera.

FIG. 2 is a block diagram of an example system for measuring visual acuity using a VR headset, and in particular one that has an eye tracker camera 2 aimed at an eye of the wearer (also referred to here as an eye tracking headset). The eye tracker camera 2 is an imaging device whose image data can be processed by eye tracking software (that may be executed by a processor in the VR headset) to measure movement of the wearers eye and track the direction of their gaze in real-time. With the addition of electronics referred to here as eye movement interpretation logic that processes the image data produced by the eye tracker camera, the system enables hands-free feedback from the wearer of the headset during visual acuity testing. This is in contrast to the example VR headset shown in FIG. 7 and described further below which can also perform visual acuity testing but with manual or audible wearer feedback, as it does not have an eye tracker camera.

Integrated within a headset housing of the system in FIG. 2 is an illumination source 3, such as one or more near infrared, NIR, light emitting diodes that produces NIR light, which illuminates an eye of the wearer of the headset as shown. This NIR light is reflected off the eye and then travels through a lens 8, followed by being reflected off a first dichroic filter 11 in the direction of an imaging lens 7 that forms an NIR image for pick up by the eye tracker camera 2. In doing so, the reflected NIR light passes through a second dichroic filter 12, to be described below.

The first dichroic filter 11 is angled relative to a path taken by visible light that is emitted from a first display 4 and that passes through the first dichroic filter 11, before impinging on the eye. The first display 4 may be a main display of the headset, which serves to present virtual reality images to the eye. The first dichroic filter 11 is also angled so that it can reflect the NIR light that has been reflected from the eye, towards the second dichroic filter 12. The second dichroic filter 12 is positioned to pass the reflected NIR light from the first dichroic filter 11 towards the eye tracker camera 2, but it is also angled relative to that path so as to reflect visible light emitted from a second display 6 towards the first dichroic filter 11. The second display 6 may be a micro display. More generally, a display surface of the first display 4 may be at least two times larger than that of the second display 6, and the first display 4 has at least twice the full frame pixel count of the second display 6. The first display 4 may for example have a full frame pixel count of 1920× 1080 pixels or more, while the second display 4 may for example have a full frame pixel count of less than 2000 pixels, e.g., 60×32 dots, or even less than 1000 pixels. As explained next, the smaller and lower pixel count of the second display 6 enables a low cost solution for visual acuity testing at 20/20 vision or better. Central visual acuity testing using a variation of the typical Snellen test or Random E test (that is adapted to the distance between the eye and the second display 6 within a VR headset) can be performed using the smaller and lower pixel count second display 6. This capability would be in addition to a number of other ophthalmic examinations that would be performed using the VR headset, and in particular using the larger, first display 4 to display patterns for those other examinations.

Figure 3:
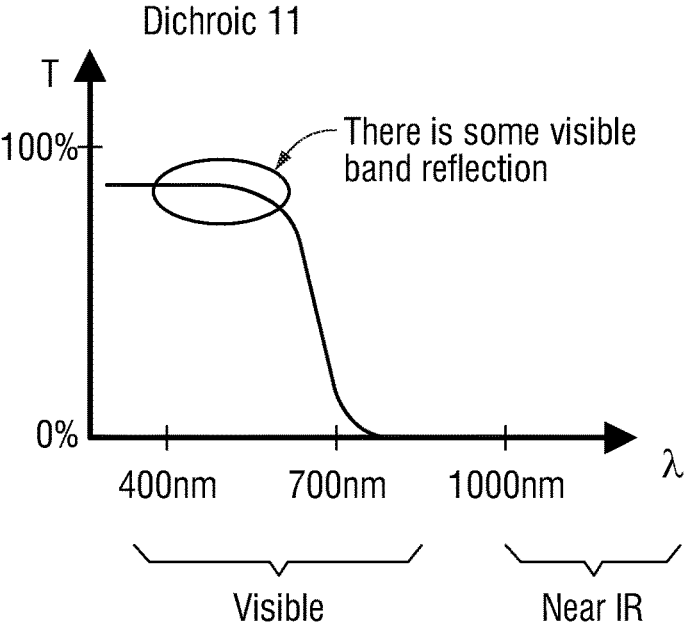
FIG. 3 illustrates an example transmission spectrum for the first dichroic filter used in the system of FIG. 2.

In one aspect of the disclosure here, the system in FIG. 2 operates based on the fact that the first dichroic filter 11 while having primary or strong transmission in the visible spectrum also exhibits a weak or small amount of reflection (in the visible spectrum.) This small reflection in the visible spectrum may be enough to direct a testing pattern that is emitted from the second display 6 to be seen by the eye of the wearer. FIG. 3 shows an example transmission spectrum for the first dichroic filter 11. This transmission is not 100% or perfect as indicated, because there is some relatively small amount of visible band reflection. For example, the visible band reflection may be more than zero but less than ten percent reflection, across a full range of visible colors, e.g., in the visible spectrum spanning from 380 nm to 700 nm. In another example of the transmission spectrum in FIG. 3, the first dichroic filter 11 would exhibit between five percent to ten percent reflection of the visible light. As to the NIR band, FIG. 3 also shows how the first dichroic filter 11 has almost no transmission in the NIR region, as NIR is being strongly reflected.

Figure 4:
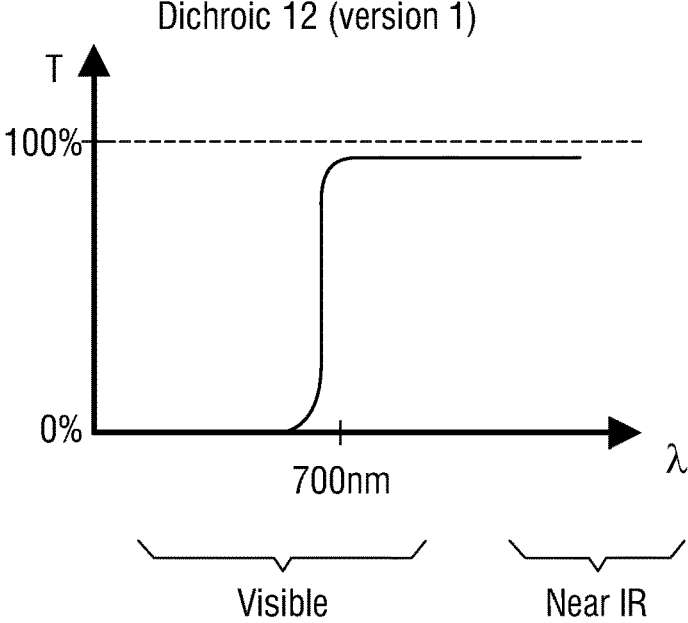
FIG. 4 shows an example transmission spectrum for a first version of the second dichroic filter used in a first version of the system of FIG. 2.

FIG. 4 shows an example transmission spectrum for a first version of the second dichroic filter 12, that works in a first version of the system exactly as shown in FIG. 2. In this first version, the second dichroic filter 12 exhibits almost no transmission (or almost perfect reflection) of the full range of visible colors up to about 700 nm, but then almost complete transmission in the NIR region.

Figure 5:
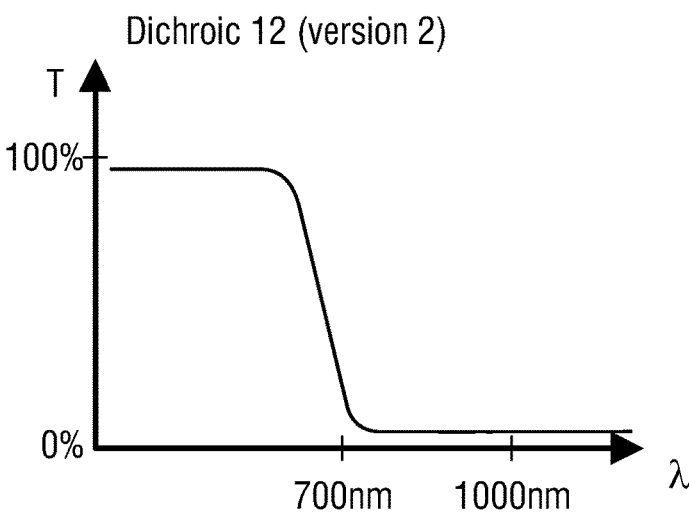
FIG. 5 shows an example transmission spectrum for a second version of the second dichroic filter used in a second version of the system of FIG. 2.

FIG. 5 shows an example transmission spectrum for another version of the second dichroic filter 12 that is suitable for use in another version of the system of FIG. 2. In this other version of the system, the locations of the second display 6 and the eye tracker camera 2 are swapped relative to how they are shown in FIG. 2. As a result, the transmission spectrum of the second version of the second dichroic filter 12 is flipped about approximately 700 nm, relative to the first version shown in FIG. 4: the second version reflects NIR light (from the first dichroic filter 11 towards the eye tracker camera 2), and passes the full range of visible light (from the second display 6 to the first dichroic filter 11.)

Still referring to the system in FIG. 2, given that the visible band reflection characteristic of the first version of the first dichroic filter 11 shown in FIG. 3 is weak (relative to its visible band transmission characteristic), the testing pattern produced by the second display 6 might be difficult to see for the wearer. As a result, there may be a need to darken the first display 4 while the second display 6 is active, to improve the ability of the wearer to see the testing pattern that is being produced by the second display 6. For this reason, pixel data control circuitry may be added as shown in FIG. 2, that is coupled to darken the first display 4 while simultaneously activating the second display 6 to display the pattern for visual acuity testing. This would be in response to a first visual acuity test selection whose image pattern may be designed for testing 20/20 vision or better which may require use of the second display 6. However, when testing for 20/40 vision, 20/60 vision, or worse, the first display 4 may be better than the second display 6 at showing larger patterns: in that case, the pixel data control circuitry may darken the second display 6 while simultaneously activating the first display 4 to display a pattern for testing 20/40 vision or worse. The term "darken" as used here means to power off the display, activate the display with only black pixels in the full frame, or activate the display to show a pixel pattern that is dark enough to not interfere with testing the wearer's visual acuity using the other display (which is showing the visual acuity test pattern.) More generally, there may be a selection between the first display 4 (e.g., a main, larger, high pixel count display) and the second display 6 (e.g., a "micro display", or smaller, low pixel count display), according to any one of two or more visual acuity test selections, and the pixel data control circuitry provides the selected display with the appropriate pixel pattern set for each test selection.

As mentioned above, in the system of FIG. 2 the first dichroic filter 11 serves to reflect toward the eye the visual acuity pattern that is being displayed by the second display 6. This visible band reflection may be across the full visible spectrum but it is a weak or small reflection, as seen in the transmission curve shown in FIG. 3. As such, the testing pattern produced by the second display 6 might be difficult to see by the wearer due to a ghosting effect that arises from the weak reflection characteristic. A dichroic filter has two surfaces, and so the reflection from each of these surfaces may be specified or considered in the design of the system. If the dichroic filter is thin, e.g., effectively a 'pellicle', or the second surface is assumed to be perfectly anti-reflection, AR, coated, then advantageously an undesired and offset 'ghost' reflection may not be evident to the wearer of the headset.

Figure 6:
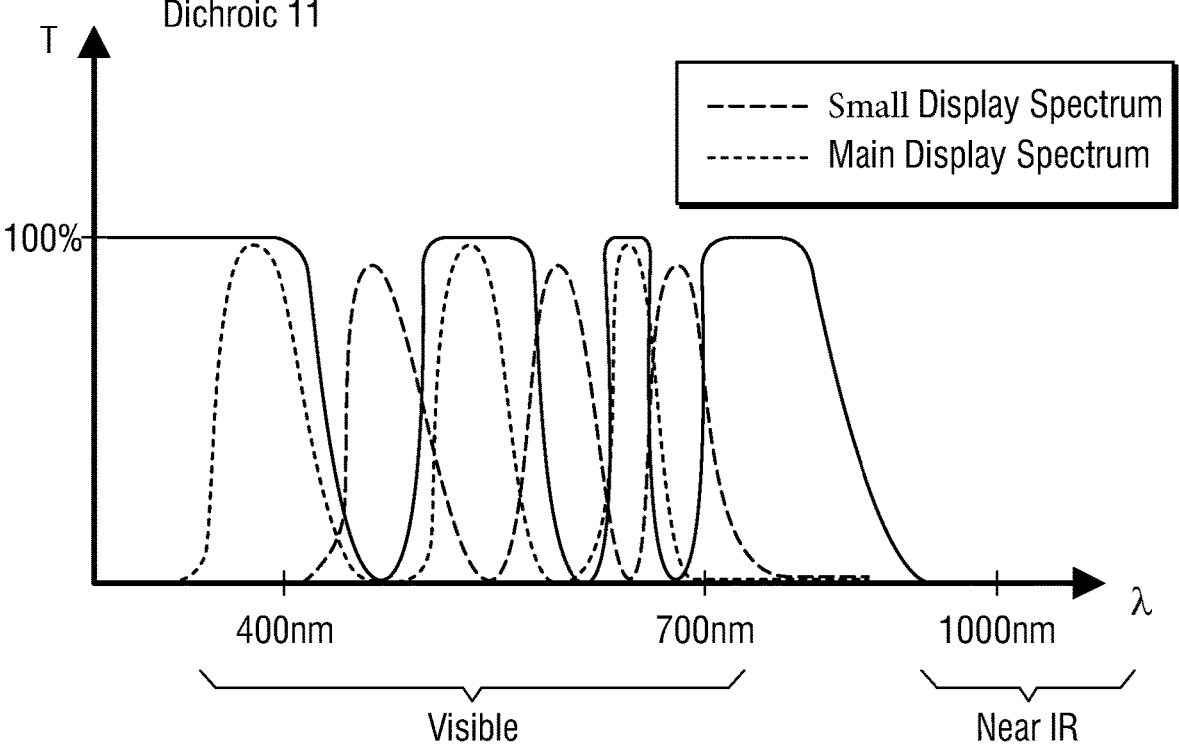
FIG. 6 shows an example transmission spectrum for another version of the first dichroic filter.

To address the ghosting problem, FIG. 6 shows an example transmission spectrum for another version of the first dichroic filter 11 (that is suitable for use in both versions of the system of FIG. 2.) This second version of the dichroic filter 11 enables the image produced by the second display 6 to be reflected with greater fidelity (than would be achieved using the transmission spectrum shown in FIG. 3.) Here, the transmission characteristic in the visible spectrum is not "uniform" across the full visible range, but instead varies in a way that exhibits notches. In other words, the transmission characteristic has a bandpass characteristic; it contains several pass bands which are aligned with the discrete colors, respectively, that are emitted by the first display 4. The transmission notches are regions in which the dichroic filter 11 reflects strongly (e.g., at least 50%.)

In the example shown in FIG. 6, the first dichroic filter 11 has three pass bands that are aligned with a first visible color being a shade of blue, a second visible color being a shade of green, and a third visible color being a shade of red, respectively. Those are a common set of primary, visible band colors that are emitted by the first display 4 when producing a full color or black and white image. The first display 4 may be implemented as an organic light emitting diode display that has a color filter array or color filter method having those three primary colors. Tuning the transmission characteristic of the first dichroic filter 11 in this manner results in strong transmission (by the first dichroic filter 11) of the image produced by the first display 4.

Now, in order to also achieve strong reflection (by the first dichroic filter 11) of the visible image produced by the second display 6, the second display 6 may also be implemented as one that emits in generally the same primary or discrete colors as the first display 4, but those primary colors are slightly shifted (in wavelength) relative to the primary colors emitted by the first display 4. More generally, the color filter array (method) of the second display 4 may have a fourth visible color, a fifth visible color and a sixth visible color, which in the example of FIG. 6 are different shades of blue, green and red, respectively. As seen in FIG. 6, these colors are aligned with the notch bands of the transmission characteristic of the first dichroic filter 11, which results in strong reflection (by the first dichroic filter 11) of the visible band image produced by the second display 6. Of course, the choice of RGB colors shown in FIG. 6 is only an example— the concept is also applicable to displays that might emit in a different combination of primary colors. As a dichroic filter can also have a polarization dependent transmission and reflection profile, the headset can be designed to optimally account for this. The first display's polarization state will likely not be modified as it is the primary display for the headset, however a polarizer and/or waveplate could be placed in the path of the image output from the second display to optimize the reflection of the second display's output from the first dichroic filter 11.

Figure 7:
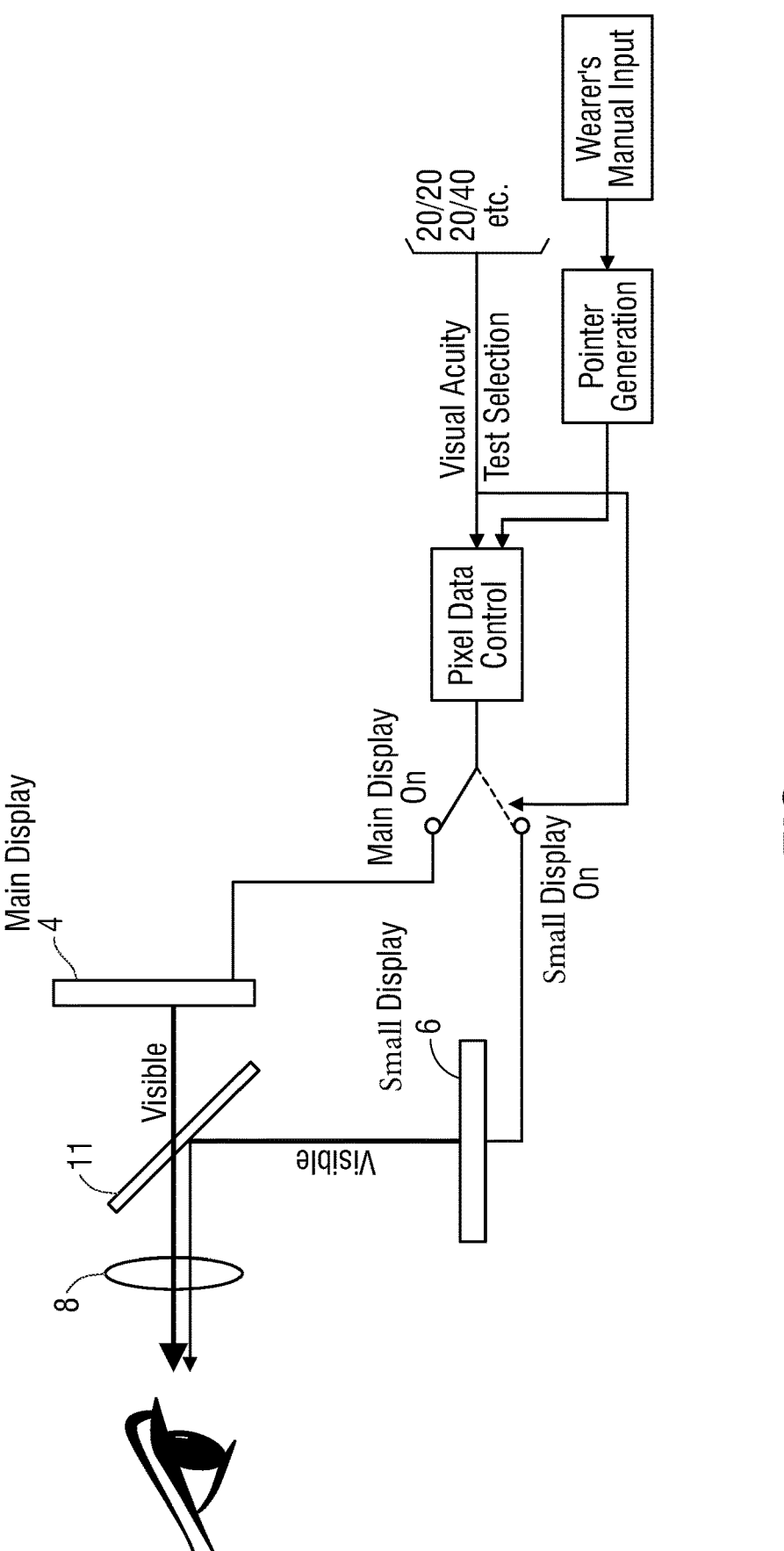
FIG. 7 is a block diagram of an example system for measuring visual acuity using a VR headset that does not have an eye tracker camera.

The system in FIG. 2 described above has an eye tracker camera 2 that enables hands-free feedback from the wearer, during ophthalmic examination of the eyes of the wearer. FIG. 7 is a block diagram of a system for measuring visual acuity in which the VR headset does not have the eye tracker camera 2. As such, feedback from the wearer about what they see during ophthalmic examination (while wearing the VR headset) is provided by the wearer either via manual input such as through a joystick or physical button press, or via audible input. The headset has the first display 4, the second display 6 that is smaller than the first display and has lower pixel count than the first display 4, and the first dichroic filter 11. The first dichroic filter 11 is configured and positioned to (strongly, e.g., with at least 70% transmission) pass visible light from the first display 4 toward the eye and weakly reflect, e.g., with no more than 20% reflection, or with no more than 5% reflection, the visible light from the second display 6 toward the eye. There may also be pixel data control circuitry coupled to darken the first display 4 while simultaneously activating the second display 6 to display a pattern for testing visual acuity, especially when testing for 20/20 vision, responsive to a first visual acuity test selection. Many of the other features and processes described above in connection with FIG. 3 and FIG. 6 apply to the version of the VR headset shown in FIG. 7.

In one aspect of the system described above, the first visible color and the fourth visible color are shades of blue, the second visible color and the fifth visible color are shades of green, and the third visible color and the sixth visible color are shades of red.

In another aspect, a method for visual acuity testing using the system described above includes providing a first visual acuity test selection that darkens the first display while simultaneously activates the second display to display a pattern for testing visual acuity. The first visual acuity test selection may be for testing 20/20 vision or better. In one variation, a second visual acuity test selection is provided that darkens the second display while simultaneously activating the first display to display a pattern for testing 20/40 vision or worse. In another variation, the second visual acuity test selection darkens the second display while simultaneously activating the first display to display a pattern for testing 20/60 vision or worse.

While certain aspects have been described and shown in the accompanying drawings, it is to be understood that such are merely illustrative of and not restrictive on the broad invention, and that the invention is not limited to the specific constructions and arrangements shown and described, since various other modifications may occur to those of ordinary skill in the art. The description is thus to be regarded as illustrative instead of limiting.

What is claimed is:

1. A system for measuring visual acuity, the system comprising:

an eye tracker camera;

an illumination source to produce near infrared, NIR, light that illuminates an eye of a user of the system;

a first display;

a first dichroic filter positioned to pass visible light from the first display to the eye, and reflect NIR light that has been reflected from the eye;

a second display; and a second dichroic filter, wherein the second dichroic filter is one of:

i) a first version that is positioned to pass the reflected NIR light from the first dichroic filter to the eye tracker camera, and reflect visible light from the second display to the first dichroic filter; or ii) a second version that is positioned to reflect the reflected NIR light from the first dichroic filter toward the eye tracker camera, and pass visible light from the second display to the first dichroic filter.

2. The system of claim 1 wherein the first dichroic filter has more than zero but less than ten percent reflection of visible light across a full range of visible colors.

3. The system of claim 2 wherein the first dichroic filter has more than five percent reflection of visible light.

4. The system of claim 1 wherein:

the first display comprises a color filter array having a first visible color, a second visible color and a third visible color, the first dichroic filter having a plurality of pass bands that are aligned with the first visible color, the second visible color and the third visible color, respectively, and the second display comprises a color filter array having a fourth visible color, a fifth visible color and a sixth visible color, the first dichroic filter having a plurality of notch bands that are aligned with the fourth visible color, the fifth visible color and the sixth visible color, respectively.

5. The system of claim 4 wherein the first visible color and the fourth visible color are shades of blue, the second visible color and the fifth visible color are shades of green, and the third visible color and the sixth visible color are shades of red.

6. The system of claim 1 with the second dichroic filter being the first version and not the second version.

7. The system of claim 1 with the second dichroic filter being the second version and not the first version.

8. The system of claim 1 wherein a display surface of the first display is at least two times larger than that of the second display, and the first display has at least twice a full frame pixel resolution of the second display.

9. The system of claim 1 further comprising:

pixel data control circuitry coupled to darken the first display while simultaneously activating the second display to display a pattern for visual acuity testing, responsive to a first visual acuity test selection.

10. The system of claim 9 wherein the first visual acuity test selection is for testing 20/20 vision or better.

11. The system of claim 10 wherein the pixel data control circuitry darkens the second display while simultaneously activating the first display to display a pattern for testing 20/40 vision or worse, responsive to a second visual acuity test selection.

12. The system of claim 10 wherein the pixel data control circuitry darkens the second display while simultaneously activating the first display to display a pattern for testing 20/60 vision or worse, responsive to a second visual acuity test selection.

13. The system of claim 9 wherein the pixel data control circuitry darkens the second display while simultaneously activating the first display to display a pattern for testing visual acuity, responsive to a second visual acuity test selection.

14. The system of claim 1 wherein the system is an eye tracking virtual reality headset, the system further comprising:

eye movement interpretation logic that processes image data produced by the eye tracker camera to detect hands-free feedback from the user of the system during visual acuity testing.

15. The system of claim 1 wherein the second display has a full frame pixel resolution of less than 1000 pixels.

16. A system for measuring visual acuity, the system comprising:

a first display;

a second display that is smaller than the first display and has lower full frame pixel resolution than the first display;

a dichroic filter positioned to pass visible light from the first display toward an eye and reflect visible light from the second display toward the eye, wherein the dichroic filter is adapted to pass a majority of the visible light incident from the first display while reflecting a minority of the visible light incident from the second display that has the lower full frame pixel resolution; and pixel data control circuitry coupled to darken the first display while simultaneously activating the second display to display a pattern for testing visual acuity, responsive to a first visual acuity test selection.

17. The system of claim 16 wherein a display surface of the first display is at least two times larger than that of the second display, and the first display has at least twice a full frame pixel resolution of the second display.

18. The system of claim 16 wherein the dichroic filter has more than zero but less than ten percent reflection of visible light across a visible spectrum spanning 380 to 700 nanometers.

19. The system of claim 18 wherein the dichroic filter has more than five percent reflection of visible light.

20. The system of claim 16 wherein:

the first display comprises a color filter array having a first visible color, a second visible color and a third visible color, the dichroic filter having a plurality of pass bands that are aligned with the first visible color, the second visible color and the third visible color, respectively, and the second display comprises a color filter array having a fourth visible color, a fifth visible color and a sixth visible color, the dichroic filter having a plurality of notch bands that are aligned with the fourth visible color, the fifth visible color and the sixth visible color, respectively.

* * * * *